United States Patent
Yan et al.

(10) Patent No.: US 11,763,234 B2
(45) Date of Patent: Sep. 19, 2023

(54) LOCATION-BASED RISK EVALUATION

(71) Applicant: International Business Machines Corporation, Armonk, NY (US)

(72) Inventors: Shunguo Yan, Austin, TX (US); Su Liu, Austin, TX (US); Andrew J. Lavery, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/022,171

(22) Filed: Sep. 16, 2020

(65) Prior Publication Data
US 2022/0083932 A1   Mar. 17, 2022

(51) Int. Cl.
| G06Q 10/0635 | (2023.01) |
| G16H 50/30 | (2018.01) |
| G06Q 50/26 | (2012.01) |
| G06Q 10/0637 | (2023.01) |
| G06Q 10/1093 | (2023.01) |
| G16H 50/80 | (2018.01) |

(52) U.S. Cl.
CPC ..... *G06Q 10/0635* (2013.01); *G06Q 10/0637* (2013.01); *G06Q 10/1095* (2013.01); *G06Q 50/265* (2013.01); *G16H 50/30* (2018.01); *G16H 50/80* (2018.01)

(58) Field of Classification Search
None
See application file for complete search history.

(56) References Cited

U.S. PATENT DOCUMENTS

| 11,087,886 B1 * | 8/2021 | Brown | G16H 50/80 |
| 2007/0122003 A1 * | 5/2007 | Dobkin | G08B 13/19645 340/506 |
| 2009/0312660 A1 * | 12/2009 | Guarino | A61B 5/113 600/529 |
| 2016/0148133 A1 * | 5/2016 | Haggar | G06Q 10/063112 705/7.14 |

(Continued)

FOREIGN PATENT DOCUMENTS

| CA | 3104823 A1 * | 1/2020 | G06F 1/3231 |
| CN | 111311018 A | 6/2020 | |

(Continued)

OTHER PUBLICATIONS

Peters, Debra PC, et al. "Cross-scale interactions, nonlinearities, and forecasting catastrophic events." Proceedings of the National Academy of Sciences 101.42 (2004): 15130-15135. (Year: 2004).*

(Continued)

*Primary Examiner* — Thomas L Mansfield
(74) *Attorney, Agent, or Firm* — Kelsey M. Skodje (57) ABSTRACT

An event at a location is identified. An event risk of the event can be calculated based on risk characteristics of both the location of the event ("location risk characteristics") and the event itself ("personnel risk characteristics"). Location risk characteristics can include a visitor history of the location. Personnel risk characteristics can be based on attendees of the event, such as a number of attendees. The overall event risk, once calculated, can be compared to a threshold. Depending on the comparison, a risk mitigation policy can be implemented.

20 Claims, 6 Drawing Sheets

(56) References Cited

U.S. PATENT DOCUMENTS

| | | | |
|---|---|---|---|
| 2016/0163186 A1* | 6/2016 | Davidson | G06Q 10/0635 340/506 |
| 2018/0052970 A1* | 2/2018 | Boss | G16H 50/30 |
| 2018/0107802 A1* | 4/2018 | Satterwhite | G16H 50/80 |
| 2018/0150600 A1* | 5/2018 | Astigarraga | G06Q 50/14 |
| 2018/0150601 A1* | 5/2018 | Astigarraga | G16H 50/80 |
| 2018/0308585 A1 | 10/2018 | Holmes et al. | |
| 2019/0122759 A1 | 4/2019 | Wakimoto | |
| 2021/0004910 A1* | 1/2021 | Trundle | G06Q 40/08 |
| 2022/0005298 A1* | 1/2022 | Shen | G01K 13/20 |

FOREIGN PATENT DOCUMENTS

| | | | |
|---|---|---|---|
| WO | WO-2009150282 A2 * | 12/2009 | G06F 17/5018 |
| WO | 2017216056 A1 | 12/2017 | |
| WO | WO-2021222978 A1 * | 11/2021 | |

OTHER PUBLICATIONS

Dubois, Amandine, and Jean-Pierre Bresciani. "Person identification from gait analysis with a depth camera at home." 2015 37th Annual International Conference of the IEEE Engineering in Medicine and Biology Society (EMBC). IEEE, 2015. (Year: 2015).*

Kumar, Aishwarya, Puneet Kumar Gupta, and Ankita Srivastava. "A review of modern technologies for tackling COVID-19 pandemic." Diabetes & Metabolic Syndrome: Clinical Research & Reviews 14.4 (2020): 569-573. (Year: 2020).*

Kvapilova, Lucia, et al. "Continuous sound collection using smartphones and machine learning to measure cough." Digital biomarkers 3.3 (2019): 166-175. (Year: 2019).*

Hwang, Tzung-Jeng, et al. "Loneliness and social isolation during the COVID-19 pandemic." International psychogeriatrics 32.10 (2020): 1217-1220. (Year: 2020).*

World Health Organization. Overview of public health and social measures in the context of COVID-19: interim guidance, May 18, 2020. No. WHO/2019-nCoV/PHSM_Overview/2020.1. World Health Organization, 2020. (Year: 2020).*

"Office Risk Assessment Checklist," process.st, Printed Sep. 11, 2020, 25 pages, https://www.process.st/checklist/office-risk-assessment-checklist/.

"Health Map", Printed Sep. 11, 2020, 2 pages, https://www.healthmap.org/en/.

Liao et al., "A new method for assessing the risk of infectious disease outbreak," Scientific Reports, NCBI, Jan. 9, 2017, 25 pages, doi: 10.1038/srep40084, https://www.ncbi.nlm.nih.gov/pmc/articles/PMC5220355/.

Coviello et al., "Predicting and containing epidemic risk using on-line friendship networks," Plos One, May 16, 2019, 14 pages, https://journals.plos.org/plosone/article?id=10.1371/journal.pone.0211765.

"CDC Workplace Health Resource Center," CDC Centers for Disease Control and Prevention, Last reviewed Feb. 29, 2020, 5 pages, https://www.cdc.gov/workplacehealthpromotion/initiatives/resource-center/index.html.

"Epidemics and the Workplace," Osh Wiki, Last edited Jun. 8, 2020, 13 pages, https://oshwiki.eu/wiki/Epidemics_and_the_Workplace.

"A checklist for pandemic influenza risk and impact management," World Health Organization, Global Influenza Programme, 2018 Update, 59 pages, ISBN 978-92-4-151362-3, https://www.who.int/influenza/preparedness/pandemic/PIRM_Checklist_update2018.pdf.

"Electronic bacteria sensor is potential future tool for medicine and food safety," Science Daily, Jun. 14, 2016, 3 pages, https://www.sciencedaily.com/releases/2016/06/160614100347.htm.

* cited by examiner

LOCATION-BASED RISK EVALUATION

BACKGROUND

Workplace safety is a top priority for many employers. Most workplaces have some degree of safety policy in effect, and many workplaces are equipped with various safety monitoring systems to help support safety efforts. Such systems might, for example, monitor employee (or customer/visitor) movements or behaviors, track density of people in various rooms (such as to monitor fire safety compliance), detect unsafe behaviors (such as violating vehicle top speeds), etc. This monitoring may be performed with a number of sensors such as cameras, motion trackers, security checkpoints, and the like.

SUMMARY

Some embodiments of the present disclosure can be illustrated as a method. The method includes calculating location risk characteristics of a location, the location risk characteristics including a visitor history of the location. The method further comprises identifying an event at the location. The method further comprises calculating personnel risk characteristics of the event, the personnel risk characteristics including a number of attendees of the event. The method further comprises calculating an event risk based on the location risk characteristics and on the personnel risk characteristics. The method further comprises acquiring a risk acceptability threshold. The method further comprises comparing the event risk to the risk acceptability threshold. The method further comprises implementing a risk mitigation policy based on the comparison.

Some embodiments of the present disclosure can also be illustrated as a computer program product comprising a computer readable storage medium having program instructions embodied therewith, the program instructions executable by a computer to cause the computer to perform the method discussed above.

Some embodiments of the present disclosure can be illustrated as a system. The system may comprise memory and a central processing unit (CPU). The CPU may be configured to execute instructions to perform the method discussed above.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure. Features and advantages of various embodiments of the claimed subject matter will become apparent as the following Detailed Description proceeds, and upon reference to the drawings, in which like numerals indicate like parts, and in which:

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to systems and methods to evaluate and mitigate risk at a location. More particular aspects relate to a system to calculate location risk characteristics of a location, personnel risk characteristics of an event at the location, and an event risk, and compare the event risk to a threshold, implementing one or more risk mitigation policies based on the comparison.

While many health and safety programs exist throughout the modern workplace, they are often tailored to a specific issue, such as a specific disease or safety concern. However, such programs are often ineffective against threats they are not specifically designed to mitigate, particularly unknown threats. Systems and methods consistent with the present disclosure enable proactive analysis and mitigation of health risks in various locations without knowledge of a specific contagion or its symptoms, mechanism of infection, etc.; in other words, generalized risk of spread of infectious disease (such as a new epidemic or pandemic) at a location can be analyzed and mitigated.

As described herein, an "event" at a "location" has an associated overall "event risk" representing a risk of some negative outcome (e.g., an attendee becoming ill, injury, etc.). This event risk has multiple contributing factors that are each calculated. For example, the location of the event has associated "location risk characteristics" (calculated based upon, for example, visitor history and/or layout of the location) and the event itself has an associated "personnel" risk (calculated based upon, for example, a number of attendees of the event).

Figure 1:
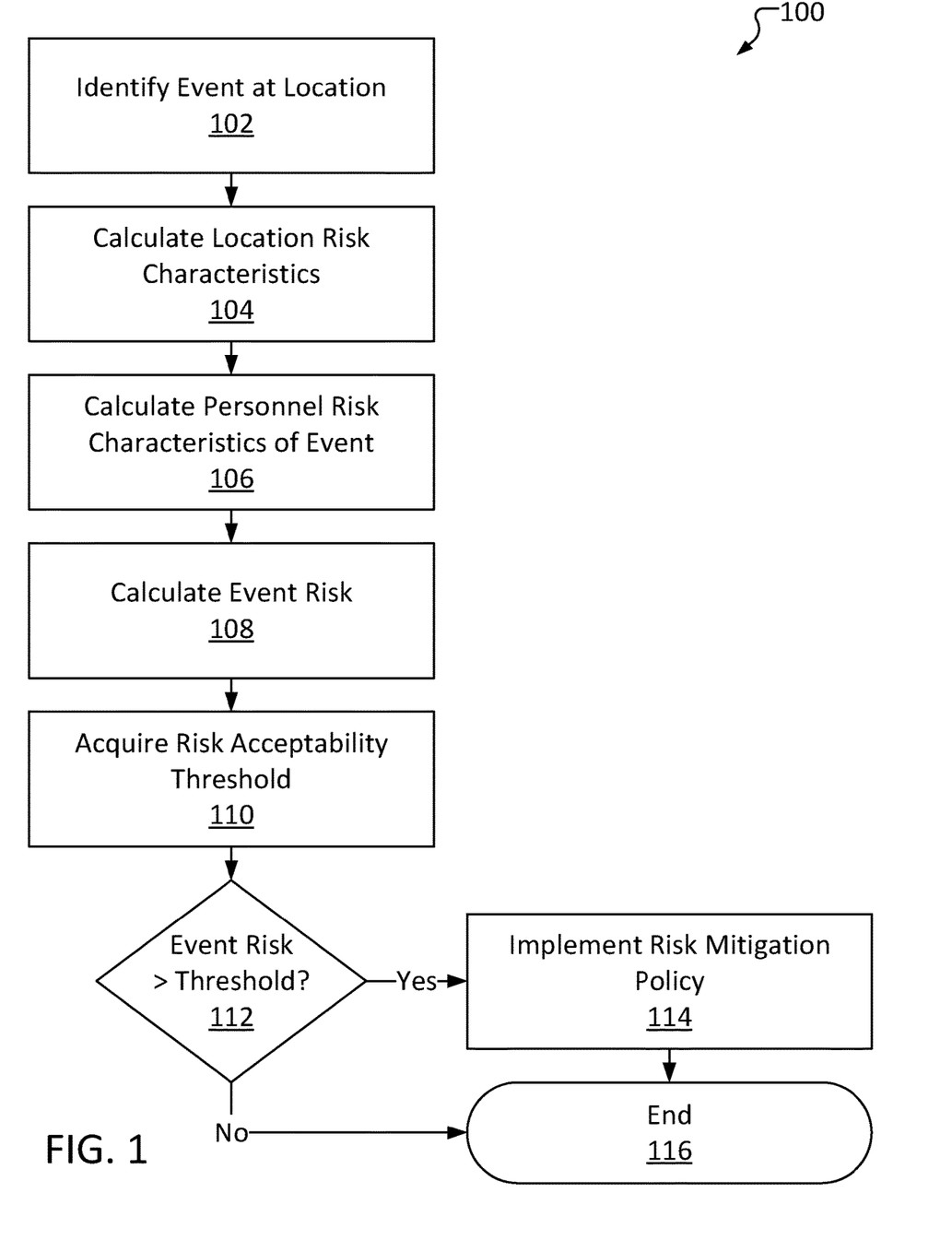
FIG. 1 is a high-level event risk evaluation and mitigation method, consistent with several embodiments of the present disclosure.

FIG. 1 is a high-level event risk evaluation and mitigation method 100, consistent with several embodiments of the present disclosure. Method 100 includes identifying an event at a location at operation 102. As used herein, an "event" may include one or more persons entering the location. A "location" could be a room, a building, or a portion of a room. The "identifying" may leverage one or more sensors, such as a camera, a turnstile, etc. For example, operation 102 may include identifying that a person is walking into a hallway. In some embodiments, the "identifying" may also include predicting a future event such as by leveraging a scheduling system; for example, operation 102 may also include receiving a request to schedule a meeting (i.e., an event) in a given room (i.e., a location). In some use cases, the "event" identified via operation 102 may be hypothetical. Hypothetical events may be identified and analyzed for purposes of assessing a current state of a location. For example, in some embodiments, method 100 may enable a system to assess whether an event consisting of a single person entering a room would constitute an unacceptable risk, thus indicating that the room should be closed/scheduled for sanitization.

Thus, method 100 further includes calculating the location risk characteristics at operation 104. Location risk characteristics may include or be calculated based on layout characteristics of the location such as, for example, a size of the location (e.g., floorspace, volume, or both), a number of doors leading into or out of the location, whether any movement restrictions are in place (such as locked doors, permanent fixtures in the location, one-way walking paths, etc.), ventilation characteristics (turnover time, number of vents, etc.), etc.

Operation 104 may also include acquiring visitor history. Visitor history, as used herein, refers to factors such as a number of people that have been present at the location, the duration during which they were present, a peak number of people, etc. In some embodiments, operation 104 may also include determining a likelihood that the location has been visited by a contagious person (or people, and for how long). This may be performed, for example, based on observing coughing, sneezing, etc., and may affect the calculated location risk characteristics. As an example, a system may receive information from one or more microphones situated at or near the location, analyzing recorded audio to determine whether one or more visitors is coughing and/or sneezing. Similar determinations can be made based upon recorded video information received from one or more cameras. In some embodiments, a system may analyze a historical list of visitors to the location and cross-reference it with a list of known ill and/or contagious people (e.g., a list of employees who are or recently were on sick leave, a list of self-identified sick people, etc.).

Method 100 further includes calculating personnel risk characteristics of the event at operation 106. Personnel risk characteristics may include or be calculated based on, for example, a number of attendees of the event. For example, at operation 102, a request to schedule a 30-person meeting (a predicted event with 30 attendees) may be identified (even if the meeting never actually occurs). In another example, a single person walking into a room is an event with a single attendee. In some embodiments, personnel risk characteristics may also be calculated based on a likelihood that one or more attendee is contagious, based on similar methods described with reference to operation 104.

Method 100 further includes calculating an event risk at operation 108. Operation 108 may include, for example, multiplying the location risk characteristics calculated at operation 104 by the personnel risk characteristics calculated at operation 106 to determine the overall event risk. Other means of calculating the event risk based on the location risk characteristics and personnel risk characteristics are also considered. For example, the location risk characteristics and personnel risk characteristics may be weighted differently from one another, they may be added instead of multiplied, etc.

Method 100 further includes acquiring a risk acceptability threshold at operation 110. A "risk acceptability threshold" describes a level of risk considered acceptable by a system performing method 100 (or an operator of the system). In some embodiments, operation 110 may include receiving/loading/utilizing a default risk acceptability threshold, such as one preloaded into a system performing method 100. The risk acceptability threshold may vary depending upon event/location. For example, a first location may be a conference room having a first risk acceptability threshold, while a second location may be a workspace of several critical employees and have a second, lower risk acceptability threshold. In some embodiments, the risk acceptability threshold may account for whether one or more attendees of the event identified at operation 102 is particularly vulnerable. For example, operation 110 may include receiving data describing a sensitivity level of an attendee of the event. This data may indicate, for example, that an attendee of the event is particularly sensitive to disease or otherwise high-risk. Similarly, this data may indicate that an attendee is particularly resilient (e.g., healthy). In some embodiments, sensitivity data may also describe non-physiological personal risk factors, such as attire (whether a person is wearing a face mask, a face shield, a hazardous materials suit), whether a person has undergone relevant training (e.g., fire safety training, hygiene training, etc.), and the like. Operation 110 may thus include calculating a specific risk acceptability threshold based upon attendees of the event.

Method 100 further includes determining whether the event risk is above the risk acceptability threshold at operation 112 (via comparison, for example). If the event risk is above the risk acceptability threshold (112 "yes"), method 100 further includes implementing a risk mitigation policy at operation 114. Operation 114 may include, for example, alerting an attendee and/or organizer of the event that the event risk is too high. As another example, the event may be a hypothetical event including a lone person entering the location. If such a hypothetical event results in an unacceptable risk level, operation 114 may include closing the location or otherwise restricting access. As an additional example, the event may comprise a meeting, identified via detecting a schedule request. In such an example, operation 114 may include proposing an alternate location. As a further example, the event may comprise use of a stairwell, elevator, and/or hallway. In such an example, operation 114 may include proposing an alternate route. Operation 114 may additionally or alternatively include rejecting a meeting request, scheduling a cleaning, proposing social guidelines (e.g., requiring attendees of the event to maintain a minimum distance from one another), etc. Operation 114 may include causing a message to be sent to a device (such as a mobile phone of an event attendee or planner), causing a message to display at or near the location, causing an audible alert to play (e.g., "this room is closed for cleaning," "high-risk stairwell—use stairwell C instead if possible"), etc.

In some embodiments, operation 114 may include adjusting a list of attendees of the event. For example, an event may include 500 attendees, one of whom may have an abnormal sensitivity level. A first risk acceptability threshold of 0.3 may be calculated accounting for the sensitive attendee. A second risk threshold of 0.5 may be calculated assuming that, for example, the 499 other attendees (i.e., all attendees except the attendee having the abnormal sensitivity level) were the only ones attending. The event risk may be calculated to be 0.4 (based on, as described above, location risk characteristics and personnel risk characteristics). Thus, the event risk may be above the first threshold but may be below a second, higher threshold. In some embodiments, in such a situation, operation 114 may include modifying a list of attendees to remove the sensitive attendee.

In some use cases, rather than directly modifying a list of attendees, operation 114 may include proposing the modification to an administrator of the group (or to the sensitive attendee). Multiple attendee list modifications can be made in this manner in order to reduce the risk acceptability threshold such that the event risk is within acceptable levels. Note that removing any attendee may also reduce the event risk itself, so removing a sensitive attendee may both raise the risk acceptability threshold and lower the event risk.

Once the risk mitigation policy is implemented, or if the event risk is below the threshold (112 "No"), method 100 ends at 114. Multiple thresholds may be implemented, with varying policies being enacted based upon which thresholds the event risk is above/below, as described in further detail below with reference to FIG. 4.

Figure 2:
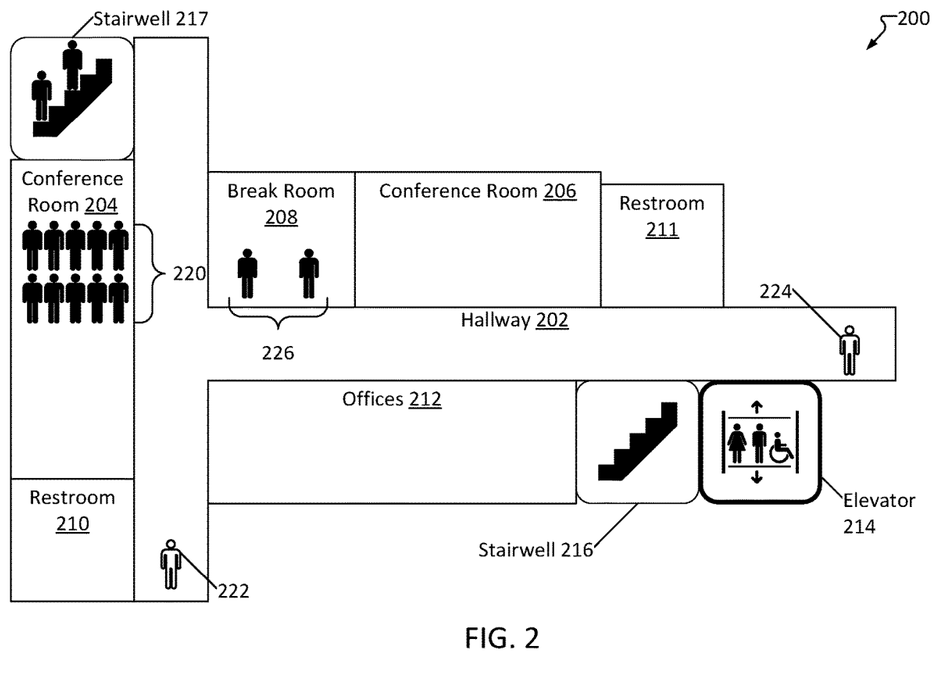
FIG. 2 is an example layout of several locations for which the embodiments of the present disclosure can be performed.

FIG. 2 is an example layout of a region 200 including several locations for which the embodiments of the present disclosure can be performed. Region 200 may include, for example, a floorplan, blueprint, or model of a building. While region 200 includes a plurality of locations such as offices 212, in some embodiments, region 200 may only include a single location (such as, for example, conference room 204). In some embodiments, a location may be broken up into a set of "sublocations," such as portions of a hallway, rooms of a building, etc. In other words, region 200 may be treated as a "location" (with its own location risk characteristics) while conference rooms 204, 206 and hallway 202 may each be treated as "sublocations" (each having their own individual location risk characteristics) within the location of region 200.

Region 200 includes a hallway 202 connecting a plurality of other locations (such as first conference room 204 and second conference room 206). Depending upon circumstances, hallway 202 could be treated as a singular location, or a set of smaller sublocations. A person (such as persons 222, 224, distinguished from visitor histories 220 and 226 by being depicted as outlines rather than solid icons) walking into hallway 202 may be considered an "event." As a further clarifying example, a person walking into conference room 204, then into hallway 202, then into break room 208 may comprise three different "events."

As an example, a person 222 heading toward stairwell 217 may be redirected to stairwell 216 due to location risk characteristics of a portion of hallway 202 (or location risk characteristics of stairwell 217 itself). Person 222's predicted entry to the portion of hallway 202 may be an event with associated personnel risk characteristics based upon person 222 as the sole attendee, and the location risk characteristics combined with the personnel risk characteristics may result in an event risk above a risk acceptability threshold, resulting in a risk mitigation policy (such as redirecting person 222) being implemented. Person 222's intended path may be identified based on, for example, person 222 being scheduled for a meeting taking place near an exit of stairwell 217 on a different floor, a trajectory of person 222's path, person 222 attempting to open a door to stairwell 217 (such as by detecting person 222 swiping a keycard or badge), etc. Person 222 may be redirected to stairwell 216 via a notification sent to a mobile device of person 222, illuminating a warning sign, etc.

Region 200 also includes a first conference room 204 and a second conference room 206. Conference room 204 is associated with a visitor history including a plurality of historical visitors 220. In other words, multiple people (220) have been in conference room 204 over a certain duration. The "duration" may be a set period, such as 4 hours, 24 hours, one week, etc., or a time elapsed since a particular starting time (such as time elapsed since a last cleaning, time elapsed since a beginning of a workday, etc.). Visitors 220 may or may not have been present in conference room 204 simultaneously; in some instances, only one person may have visited at a given time. Either way, the number of visitors 220 that have been in conference room 204 may still impact location risk characteristics of conference room 204. However, conference room 204's relatively large size may have a mitigating effect; if a smaller location such as restroom 210 had a visitor history including the same plurality of visitors 220, restroom 210 may have greater location risk characteristics due simply to its smaller size relative to conference room 204. Other factors may also contribute, such as time since the room was last cleaned, how thoroughly the room was cleaned (e.g., based on whether it was scheduled for "standard" cleaning vs. a more intense "sanitization" cleaning, etc.), ventilation characteristics (air changes per hour (ACPH), filter quality, etc.), etc.

In contrast, conference room 206 may have no visitor history (suggesting, for example, that no persons have entered or been present in conference room 206 during a particular duration, such as a time elapsed since conference room 206 was last cleaned).

Depending upon visitors 220 and layout characteristics, conference room 204 may have relatively high location risk characteristics, such that an event (such as a meeting) predicted (e.g., via a schedule request) to take place in conference room 204 may have a particularly high event risk. Thus, such an event may be subject to a risk mitigation policy (e.g., the event may be cancelled, the request may be rejected, etc.). In some instances, the risk mitigation policy may result in proposing conference room 206 as an alternate location for the meeting.

Region 200 also includes a break room 208. As shown in FIG. 2, historical visitors 226 represent a visitor history of break room 208. This history, combined with other location risk characteristics of break room 208, may result in closure of break room 208. This may occur, for example, if a hypothetical event including a single person entering break room 208 (essentially an event having best-case personnel risk characteristics) may have an event risk above a risk acceptability threshold; in other words, if the location risk characteristics effectively guarantee that any event will have an unacceptably high event risk, the location may be preemptively closed. In some embodiments, depending upon risk mitigation policy, a cleaning service may be automatically scheduled in addition to (or instead of) closure of break room 208.

Region 200 further includes restrooms 210, 211. Restrooms 210, 211 may similarly be subject to location risk characteristic calculations and risk mitigation policy effects (accelerated cleaning, temporary closure, etc.), although in some use cases, at least one of restrooms 210, 211 must remain open.

Region 200 further includes an elevator 214 and two stairwells 216, 217. In some embodiments, a stairwell with relatively greater location risk characteristics (e.g., stairwell 217) may be closed. In closing the stairwell, a notification may direct users to a different stairwell (e.g., stairwell 216). Similarly, should elevator 214's location risk characteristics be elevated to unsafe levels, elevator 214 may be closed/ subject to cleaning, redirecting would-be users of elevator 214 to one of stairwells 216, 217.

As a clarifying example, a predicted event may be a meeting having 6 attendees. A system consistent with the present disclosure may determine personnel risk characteristics of the event based on the 6 attendees. An organizer of the event may attempt to schedule the meeting for conference room 204. However, conference room 204 may have a visitor history 220 of 10 people, indicating, in this example, that 10 people have been in conference room 204 since it was last cleaned. Conference room 204's visitor history 220 may result in conference room 204 having significant location risk characteristics which, in combination with the personnel risk characteristics of the event, may result in an event risk high enough to cause the system to deny or reject the schedule attempt. Instead, a system consistent with the present disclosure may propose use of conference room 206 for the meeting, as conference room 206 has remained empty since it was last cleaned.

Figure 3:
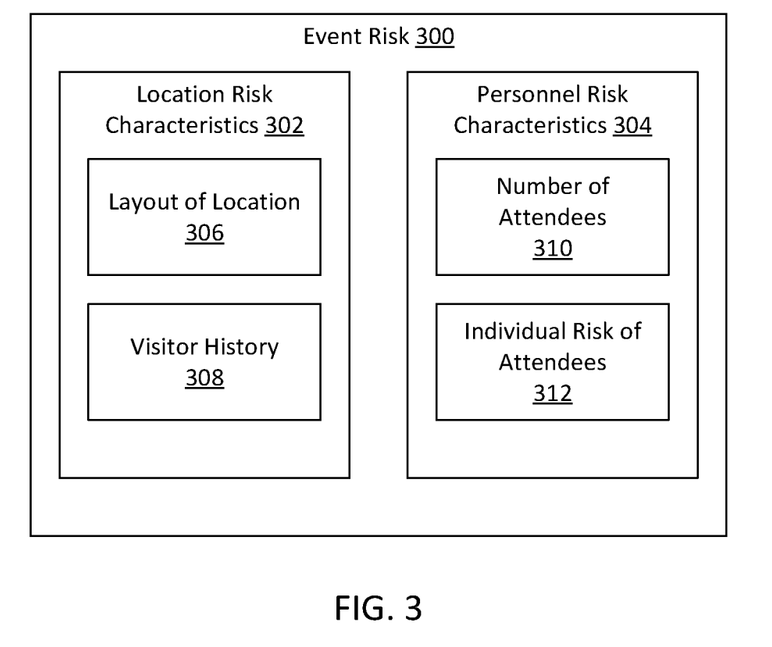
FIG. 3 is a high-level depiction of factors utilized to calculate event risk, consistent with several embodiments of the present disclosure.

FIG. 3 is a high-level depiction of factors utilized to calculate event risk 300, consistent with several embodiments of the present disclosure. As described with reference to FIG. 1, event risk 300 is calculated based on two contributing sets of factors: location risk characteristics 302 (associated with a location at which the event takes place, took place, or is predicted/hypothesized to take place) and personnel risk characteristics 304 (associated with the attendees of the event itself).

Location risk characteristics 302 include a layout of the location 306. The layout may include, for example, a number of doors, a size of the location, a volume of the location, a number of walls, an air turnover time, a number of vents, an air flow rate, etc. Location risk characteristics 302 are also based on visitor history 308. Visitor history 308 may be based on a number of people who have been in the location recently or information about the particular individuals who have recently been in the location. For example, visitor history 308 may be calculated based upon one or more visitor metrics such as a peak number of visitors during a duration, an average number of visitors over the duration, a total number of visitors during the duration, a number of times during the duration that the concurrent visitor count exceeded a particular threshold, etc. In some embodiments, visitor history 308 may account for a likelihood that one or more visitors is contagious (determined based upon observation of visitors exhibiting behaviors such as coughing, sneezing, etc. as well as possible mitigating factors such as whether the visitors are wearing face masks, etc.).

Personnel risk characteristics 304 include a number of attendees 310. Number of attendees 310 may be determined based upon observation via one or more sensors (e.g., a camera may detect three people entering a location) or from a scheduling system (e.g., a user may attempt to schedule a meeting for 3 attendees at the location). In some embodiments, personnel risk characteristics 304 may be further calculated based upon an individual risk of the attendees 312, such as a likelihood that one or more of the attendees is contagious (determined based upon observation of visitors exhibiting behaviors such as coughing, sneezing, etc.).

Figure 4:
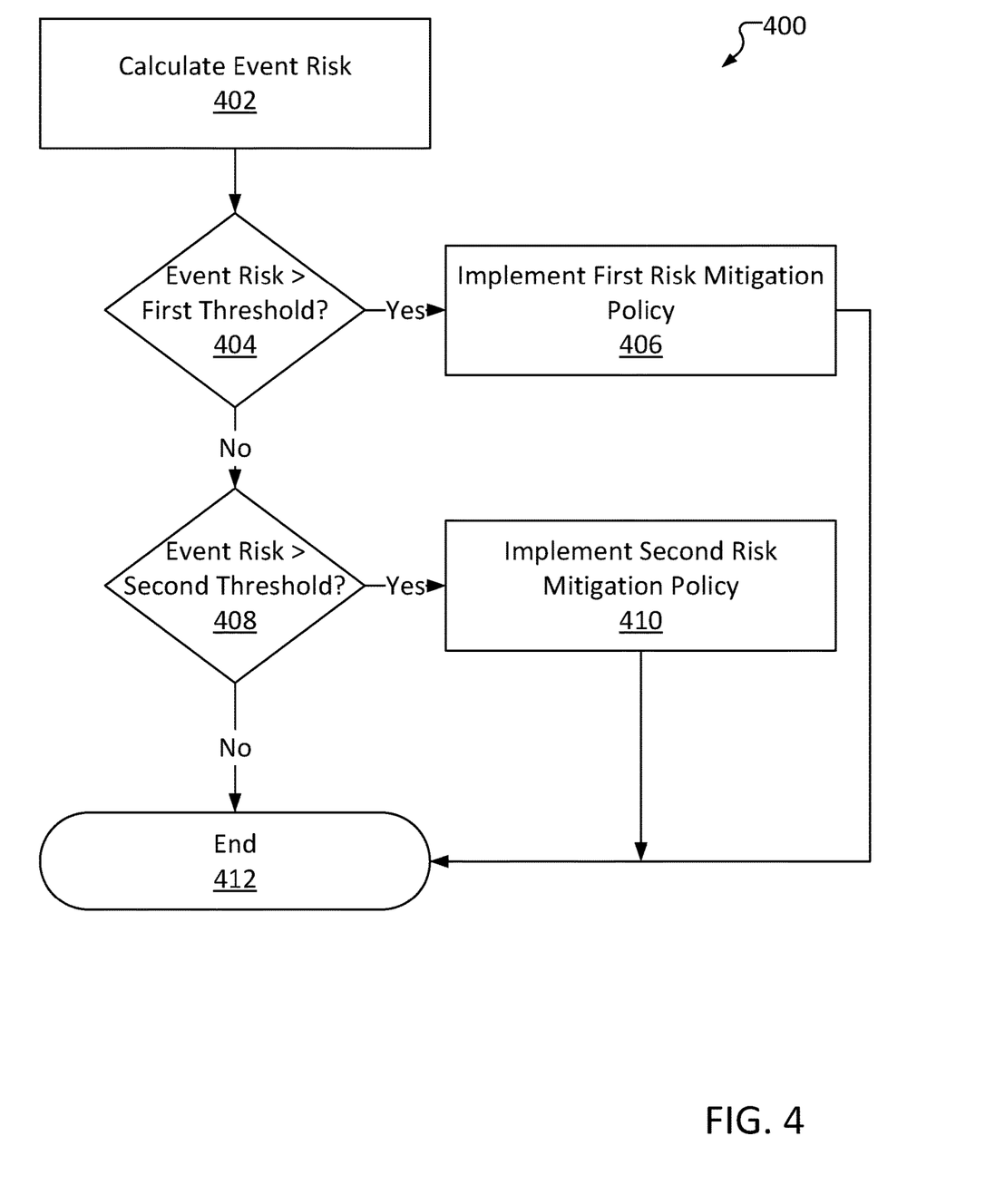
FIG. 4 is a high-level event risk mitigation method in which a risk mitigation policy can be selected from a group of two or more risk mitigation policies, consistent with several embodiments of the present disclosure.

FIG. 4 is a high-level event risk mitigation method 400 in which a risk mitigation policy can be selected from a group of two or more risk mitigation policies, consistent with several embodiments of the present disclosure. As an illustrative example, a company may have two (or more) different preset risk acceptability thresholds, each with a different associated risk mitigation policy. Thus, upon identifying an event risk of an event, a system performing method 400 may determine if the risk is above a first (higher) threshold and, if so, implement a first risk mitigation policy. Otherwise, the system may determine if the risk is above a second (lower) threshold and, if so, implement a second risk mitigation policy. Typically, the first risk mitigation policy may be more "drastic," such as closing a location, as it is implemented in response to the highest risk. However, the company may wish to have a second policy in between the drastic first policy (if risk is above the first threshold) and simply doing nothing (if risk is below the first threshold). Thus, the risk is compared to a second, lower threshold, and if it is above this second threshold, a second risk mitigation policy may be implemented, such as recommending attendees of the event practice special techniques such as maintaining a minimum distance from one another.

Method 400 includes calculating an event risk at operation 402. Operation 402 may be performed in a manner substantially similar to operation 108 of method 100, discussed above with reference to FIG. 1. As an illustrative example, a company may have multiple mitigation policies. Method 400 further includes determining whether the event risk is greater than a first risk acceptability threshold at operation 404. Operation 404 may include acquiring a first risk acceptability threshold, such as by receiving a predetermined or pre-programmed "high-risk" threshold, or by calculating one based on an identified event. Operation 404 may further include comparing the event risk to the first risk acceptability threshold.

If the event risk is above the first risk acceptability threshold (404 "Yes"), method 400 further includes implementing a first risk mitigation policy at operation 406. Operation 406 may include, for example, closing a location, ordering a cleanup or sanitization of the location, etc.

If the event risk is not above the first risk acceptability threshold (404 "No"), method 400 further includes determining if the event risk is above a second risk acceptability threshold at operation 408. Operation 408 may include, for example, acquiring a second risk acceptability threshold, such as by receiving a predetermined or pre-programmed "low-risk" threshold, or by calculating one based on an identified event. Operation 408 may further include comparing the event risk to the second risk acceptability threshold.

If the event risk is above the second risk acceptability threshold (408 "Yes"), method 400 further includes implementing a second risk mitigation policy at operation 410. Operation 410 may include, for example, restricting a number of attendees at an event, suggesting attendees of the event practice social distancing, etc. If the event risk is not above the second risk acceptability threshold (408 "No") or after operation 406 or operation 410, method 400 ends at 412. Further thresholds are also possible, as will be appreciated by a person having ordinary skill in the art.

Figure 5:
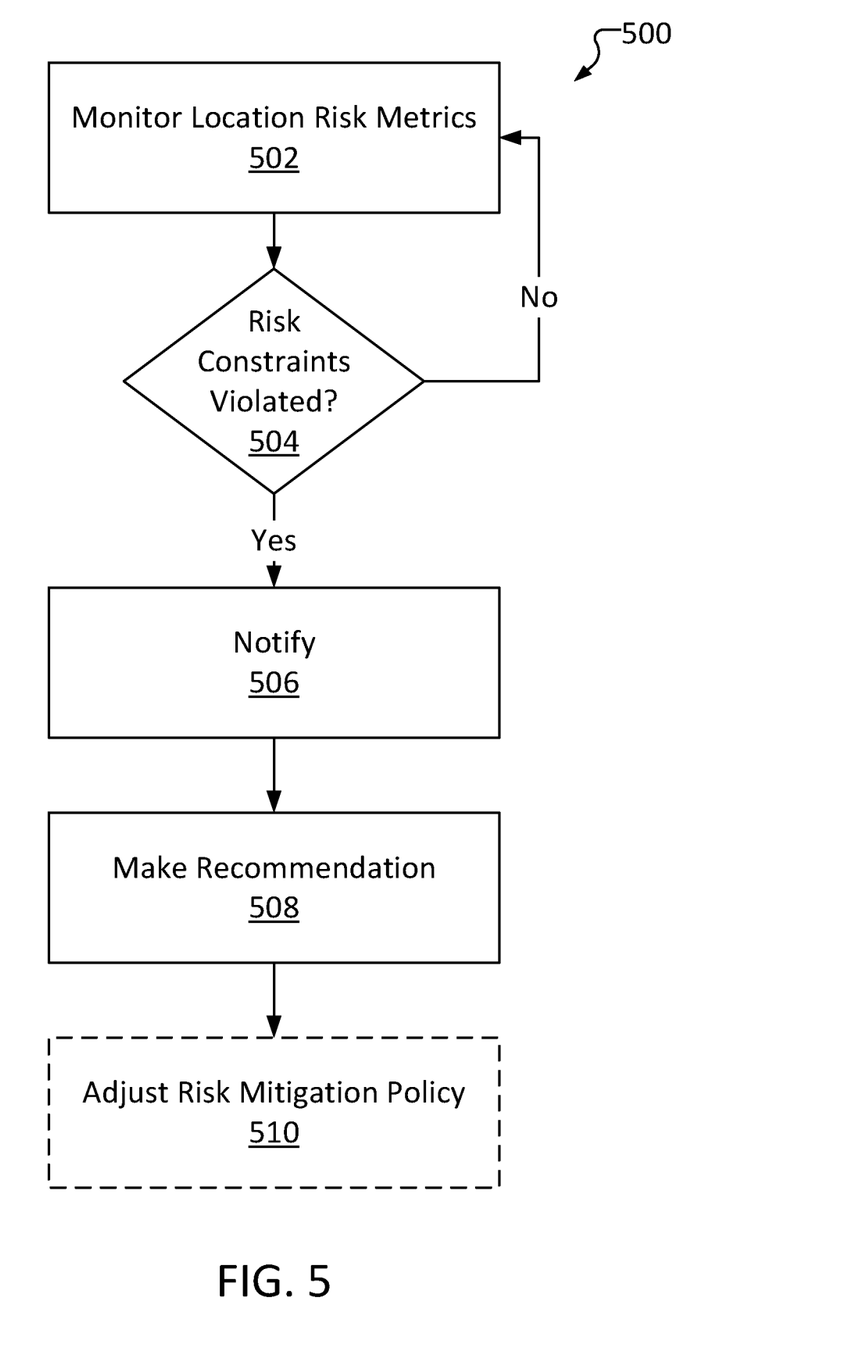
FIG. 5 is a risk monitoring and alert method, consistent with several embodiments of the present disclosure.

In addition to calculating risk and implementing risk mitigation policies, systems and methods consistent with the present disclosure may also enable monitoring overall trends and making higher-level adjustments and recommendations. For example, FIG. 5 is a risk monitoring and alert method 500, consistent with several embodiments of the present disclosure. Method 500 may enable an entity such as a business to monitor risk metrics over time, advantageously enabling analysis of impact of various risk mitigation policies. Additionally (or alternatively), method 500 may enable the business to set various risk constraints, receiving an alert whenever a constraint is violated.

Method 500 includes monitoring location risk metrics at operation 502. "Location risk metrics" may describe how location risk characteristics of a location trend over time. For example, operation 502 may include tracking visitors, determining a likelihood of whether any visitors are contagious, etc. Operation 502 may further include determining metrics of visitor counts. "Visitor metrics" may include visitor count statistics such as, for example, a peak (e.g., maximum) number of visitors. Other possible visitor metrics include an average visitor count, such as an average number of visitors present at the location at each minute since the beginning of a given day. Another possible visitor metric is a "rolling" average number of visitors, determined by periodically computing an average number of visitors present at the location for a preceding set duration (e.g., computing an average number of visitors present at the location at each minute for the last 30 minutes and updating this average every minute). In some use cases, visitor metrics may include a number of times a given threshold is met and/or exceeded, such as, for example, a number of instances the number of concurrent visitors has exceeded 20 since the beginning of a given day. In some use cases, visitor metrics may include a total number of visitors.

Method 500 further includes determining whether any risk constraints have been violated at operation 504. Risk constraints may include maximum values for the various metrics. For example, in order to protect the safety of its employees, a business may limit a number of seemingly contagious visitors (possibly including employees themselves) to a certain maximum per day (or week, etc.). As an additional example, a business may attempt to monitor effectiveness of risk mitigation policies; for example, a business may implement a staggered workday (e.g., a first group of employees may be scheduled to arrive at 8 AM and depart at 4 PM, while a second group of employees may be scheduled to arrive at 9 AM and depart at 5 PM, in order to reduce congestion at entry and exit points). Thus, upon implementing a staggered workday, a business may set a maximum (or goal) visitor rate, and perform method 500 to determine whether the staggered workday achieved the desired effect.

Operation 504 may include, for example, comparing one or more metrics determined at operation 502 to a corresponding metric constraint (a threshold comparison). Each metric may have a different constraint. If no metric constraint has been violated (504 "No"), method 500 may return to operation 502 (i.e., continuing to monitor visitor metrics).

If a visitor metric constraint has been violated (504 "Yes"), method 500 further comprises transmitting a notification at operation 506. Operation 506 may include, for example, transmitting a notification to an administrator of a system performing method 500 (e.g., by causing a signal to be transmitted to a mobile device). Operation 506 may also include causing display of an alert notification, emitting a sound, etc. In some embodiments, operation 504 may be bypassed, and operation 506 may include generating a risk report periodically or generating a risk report in response to a user request. The risk report may describe, for example, the monitored location risk characteristics.

Method 500 further comprises making a recommendation at operation 508. Operation 508 may include, for example, providing a recommendation to postpone (or accelerate) a return to a workplace (such as a return from a temporary switch to working remotely during a quarantine) based upon whether risk metrics were violated.

As an example, a company's workforce may have been relegated to working remotely due to a pandemic, a threat, or other safety/security concern, but the company may be in the process of phasing the workforce back into working at the location in "waves." The company may seek to monitor whether the risk of harm/infection at the location is exceeding allowable constraints as more waves of employees return from working remotely. If the risk is accelerating, if the risk has already exceeded safe levels, or if the risk would exceed safe levels if a change were implemented (e.g., 504 "Yes"), operation 508 may include recommending postponing a next wave of employees from returning (such as until the risk has subsided or been reduced below unsafe levels). The recommendation may be included in a risk report.

Method 500 may also comprise adjusting a risk mitigation policy at operation 510. Operation 510 may include, for example, lowering one or more risk acceptability thresholds. In some embodiments, operation 510 may include adjusting calculation of event risk. For example, a system performing method 500 may adjust a relative weight of location risk characteristics used in calculating event risk.

Figure 6:
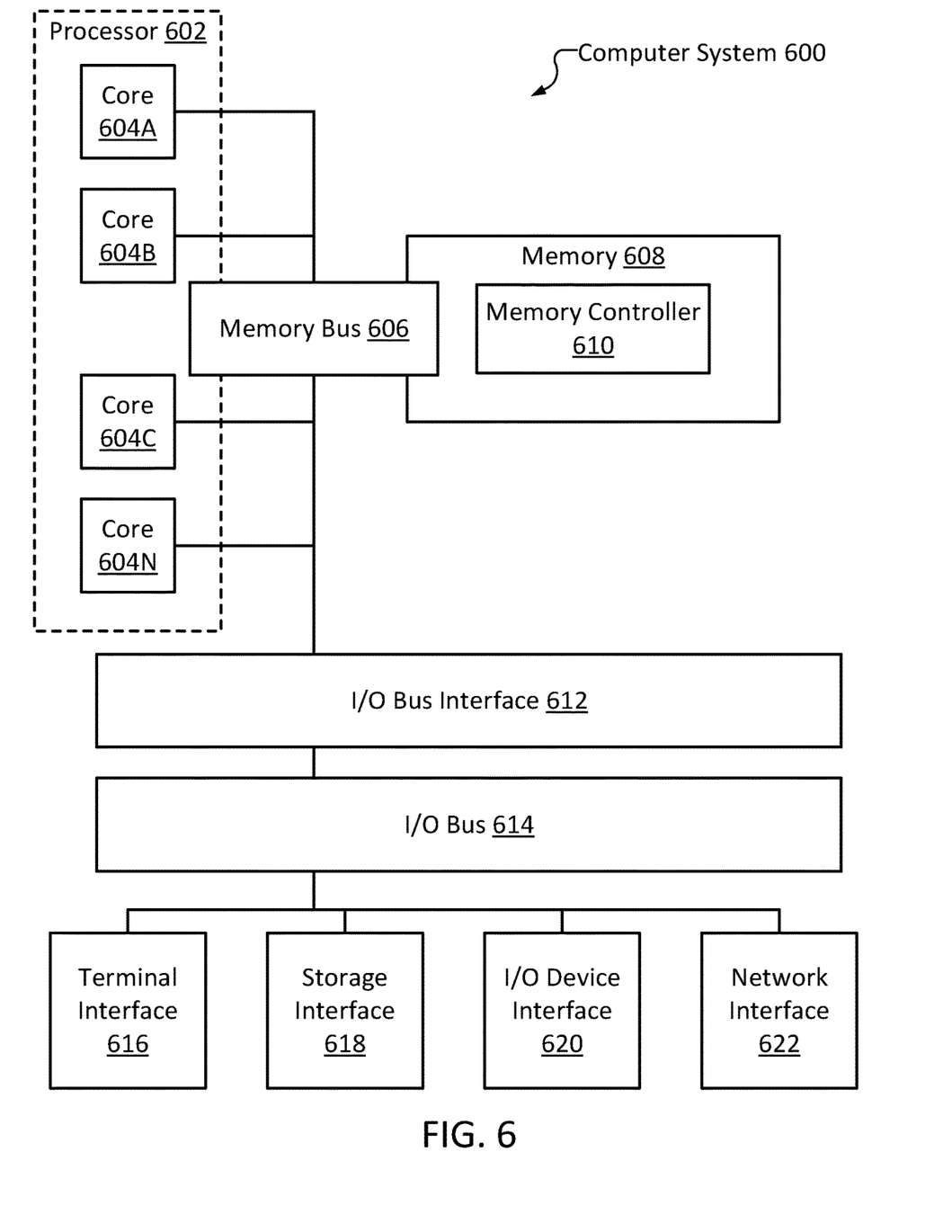
FIG. 6 illustrates a high-level block diagram of an example computer system that may be used in implementing embodiments of the present disclosure.

Referring now to FIG. 6, shown is a high-level block diagram of an example computer system 600 that may be configured to perform various aspects of the present disclosure, including, for example, methods 100, 400 and 500. The example computer system 600 may be used in implementing one or more of the methods or modules, and any related functions or operations, described herein (e.g., using one or more processor circuits or computer processors of the computer), in accordance with embodiments of the present disclosure. In some embodiments, the major components of the computer system 600 may comprise one or more CPUs 602, a memory subsystem 608, a terminal interface 616, a storage interface 618, an I/O (Input/Output) device interface 620, and a network interface 622, all of which may be communicatively coupled, directly or indirectly, for inter-component communication via a memory bus 606, an I/O bus 614, and an I/O bus interface unit 612.

The computer system 600 may contain one or more general-purpose programmable central processing units (CPUs) 602, some or all of which may include one or more cores 604A, 604B, 604C, and 604D, herein generically referred to as the CPU 602. In some embodiments, the computer system 600 may contain multiple processors typical of a relatively large system; however, in other embodiments the computer system 600 may alternatively be a single CPU system. Each CPU 602 may execute instructions stored in the memory subsystem 608 on a CPU core 604 and may comprise one or more levels of on-board cache.

In some embodiments, the memory subsystem 608 may comprise a random-access semiconductor memory, storage device, or storage medium (either volatile or non-volatile) for storing data and programs. In some embodiments, the memory subsystem 608 may represent the entire virtual memory of the computer system 600 and may also include the virtual memory of other computer systems coupled to the computer system 600 or connected via a network. The memory subsystem 608 may be conceptually a single monolithic entity, but, in some embodiments, the memory subsystem 608 may be a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures. In some embodiments, the main memory or memory subsystem 804 may contain elements for control and flow of memory used by the CPU 602. This may include a memory controller 610.

Although the memory bus 606 is shown in FIG. 6 as a single bus structure providing a direct communication path among the CPU 602, the memory subsystem 608, and the I/O bus interface 612, the memory bus 606 may, in some embodiments, comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 612 and the I/O bus 614 are shown as single respective units, the computer system 600 may, in some embodiments, contain multiple I/O bus interface units 612, multiple I/O buses 614, or both. Further, while multiple I/O interface units are shown, which separate the I/O bus 614 from various communications paths running to the various I/O devices, in other embodiments some or all of the I/O devices may be connected directly to one or more system I/O buses.

In some embodiments, the computer system 600 may be a multi-user mainframe computer system, a single-user system, or a server computer or similar device that has little or no direct user interface but receives requests from other computer systems (clients). Further, in some embodiments, the computer system 600 may be implemented as a desktop computer, portable computer, laptop or notebook computer, tablet computer, pocket computer, telephone, smart phone, mobile device, or any other appropriate type of electronic device.

It is noted that FIG. 6 is intended to depict the representative major components of an exemplary computer system 600. In some embodiments, however, individual components may have greater or lesser complexity than as represented in FIG. 6, components other than or in addition to those shown in FIG. 6 may be present, and the number, type, and configuration of such components may vary.

Embodiments of the present invention may be a system, a method, and/or a computer program product at any possible technical detail level of integration. The computer program product may include a computer readable storage medium (or media) having computer readable program instructions thereon for causing a processor to carry out aspects of embodiments of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method of monitoring, by a computer-implemented scheduling system for a region, health risks in the region, the method comprising:
   receiving, at the computer-implemented scheduling system, a floorplan defining the region and locations within the region;
   automatically monitoring, by the computer-implemented scheduling system, risk levels in each of the locations, wherein the monitoring comprises:
      receiving, at the computer-implemented scheduling system, sensor data from sensors in the region, wherein the sensors comprise cameras, motion sensors, and microphones;
      generating, by the computer-implemented scheduling system and based on the sensor data, location risk characteristics for the locations;
      continuously updating, by the computer-implemented scheduling system and based on the received sensor data, the generated location risk characteristics; and
      generating, by the computer-implemented scheduling system and based on the continuously tracked location risk characteristics, location risk metrics for each of the locations;
   determining, by the computer-implemented scheduling system and based on the location risk metrics, that a risk level for a location is above a first risk acceptability threshold;
   in response to the determining that the risk level for the location is above the first risk acceptability threshold, automatically implementing, by the computer-implemented implemented scheduling system, a first risk mitigation policy;
   receiving, at a user interface of the computer-implemented scheduling system, a scheduling request for an event in the region, the scheduling request comprising a time of the event, a location selected from the locations, and a list of predicted attendees of the event;
   in response to the scheduling request, automatically evaluating, by the computer-implemented scheduling system, potential risks associated with the event, the automatically evaluating comprising:
      identifying, via the computer-implemented scheduling system and based on the monitoring, location risk metrics for the selected location;
      generating, via the computer-implemented scheduling system and based on the list of predicted attendees, personnel risk characteristics of the event, wherein the personnel risk characteristics include a number of the predicted attendees and sensitivity levels of one or more of the predicted attendees;
      calculating, via the computer-implemented scheduling system and based on the location risk characteristics and on the personnel risk characteristics, an event risk;
      automatically adjusting, by the computer-implemented scheduling system, the first risk acceptability threshold based on the sensitivity levels; and
      determining, via the computer-implemented scheduling system, that the event risk is higher than the adjusted risk acceptability threshold; and
   automatically implementing, via the computer-implemented scheduling system, a second risk mitigation policy in response to the determining that the event risk is higher than the adjusted risk acceptability threshold, wherein the implementing comprises:
      modifying the scheduling request; and
      outputting a response to the scheduling request via the user interface, wherein the response includes a recommended change to the event.

2. The method of claim 1, wherein the location risk characteristics include:
   a number of visitors that have entered the location over a duration; and
   a maximum number of visitors in the location simultaneously over the duration.

3. The method of claim 1, wherein the visitor history includes a likelihood of a contagious person in the location.

4. The method of claim 1, wherein the implementing the second risk mitigation policy includes automatically denying the event request.

5. The method of claim 1, further comprising:
   determining, by the computer-implemented scheduling system and based on the location risk metrics, that a risk constraint has been violated; and
   automatically generating, by the computer-implemented scheduling system and based on the determining that the risk constraint has been violated, a risk report.

6. The method of claim 5, further comprising modifying, based on the determining that the risk metric constraint has been violated, the first risk mitigation policy.

7. The method of claim 1, wherein:
the selected location includes a plurality of sublocations; and
the location risk characteristics include, for each sublocation:
a number of entry/exit doors;
a size of the sublocation; and
ventilation characteristics of the sublocation.

8. A computer-implemented scheduling system for a region, comprising:
a memory; and
a central processing unit (CPU) coupled to the memory, wherein:
the CPU is configured to execute instructions to:
receive, at the computer-implemented scheduling system, a floorplan defining the region and locations within the region;
automatically monitor risk levels in each of the locations, wherein the automatically monitoring comprises:
receiving, at the computer-implemented scheduling system, sensor data from sensors, wherein the sensors comprise cameras, motion sensors, in the region and microphones;
generating, by the computer-implemented scheduling system and based on the sensor data, location risk characteristics for the locations;
continuously updating, by the computer-implemented scheduling system and based on the received sensor data, the generated location risk characteristics; and
generating, by the computer-implemented scheduling system and based on the continuously tracked location risk characteristics, location risk metrics for each of the locations;
determine, by the computer-implemented scheduling system and based on the location risk metrics, that a risk level for a location is above a first risk acceptability threshold;
in response to the determination that the risk level for the location is above the first risk acceptability threshold, automatically implement, by the computer-implemented scheduling system, a first risk mitigation policy;
receive, at a user interface of the computer-implemented scheduling system, a scheduling request for an event in the region, the scheduling request comprising a time of the event, a location selected from the locations, and a list of predicted attendees of the event;
identify, by the computer-implemented scheduling system and based on the monitoring, location risk metrics for the selected location;
generate, via the computer-implemented scheduling system, personnel risk characteristics of the event, wherein the personnel risk characteristics include a number of the predicted attendees of the event and sensitivity levels of one or more of the predicted attendees;
calculate, via the computer-implemented scheduling system and based on the location risk characteristics and on the personnel risk characteristics, an event risk;
automatically adjust, by the computer-implemented scheduling system, the first risk acceptability threshold based on the sensitivity levels;
determine, via the computer-implemented scheduling system, that the event risk is higher than the adjusted risk acceptability threshold; and
automatically implement, via the computer-implemented scheduling system, a second risk mitigation policy in response to the determining that the event risk is higher than the adjusted risk acceptability threshold, wherein the implementing comprises:
modifying the scheduling request; and
outputting a response to the scheduling request via the user interface wherein the response includes a recommended change to the event.

9. The system of claim 8, wherein the location risk characteristics include:
a number of visitors that have entered the location over a duration; and
a maximum number of visitors in the location simultaneously over the duration.

10. The system of claim 8, wherein the CPU is further configured to:
monitor a location risk metric;
determine, based on the location risk metrics, that a risk constraint has been violated; and
automatically generate, based on the determination that the risk metric constraint has been violated, a risk report.

11. The system of claim 10, wherein the CPU is further configured to modify, based on the determination that the risk metric constraint has been violated, the first risk mitigation policy.

12. The system of claim 8, wherein
the selected location includes a plurality of sublocations; and
the location risk characteristics include, for each sublocation:
a number of entry/exit doors;
a size of the sublocation; and
ventilation characteristics of the sublocation.

13. A computer program product, the computer program product comprising a computer readable storage medium having program instructions embodied therewith, wherein:
the program instructions are executable by a computer to cause the computer to:
receive, at a computer-implemented scheduling system for a region, a floorplan defining the region and locations within the region;
automatically monitor risk levels in each of the locations, wherein the automatically monitoring comprises:
receiving, at the computer-implemented scheduling system, sensor data from sensors in the region, wherein the sensors comprise cameras, motion sensors, and microphones;
generating, by the computer-implemented scheduling system and based on the sensor data, location risk characteristics for the locations;
continuously updating, by the computer-implemented scheduling system and based on the received sensor data, the generated location risk characteristics; and
generating, by the computer-implemented scheduling system and based on the continuously tracked location risk characteristics, location risk metrics for each of the locations;

determine, by the computer-implemented scheduling system and based on the location risk metrics, that a risk level for a location is above a first risk acceptability threshold;

in response to the determination that the risk level for the location is above the first risk acceptability threshold, automatically implement, by the computer-implemented scheduling system, a first risk mitigation policy;

receive, at a user interface of the computer-implemented scheduling system, a scheduling request for an event in the region, wherein the scheduling request includes parameters comprising a time of the event, a location selected from the locations, and a list of predicted attendees of the event;

identify, by the computer-implemented scheduling system and based on the monitoring, location risk metrics for the selected location;

calculate, by the computer-implemented scheduling system, personnel risk characteristics of the event, wherein the personnel risk characteristics include a number of the predicted attendees of the event and sensitivity levels of one or more of the predicted attendees;

calculate, by the computer-implemented scheduling system and based on the location risk characteristics and on the personnel risk characteristics, an event risk;

automatically adjust, by the computer-implemented scheduling system, the first risk acceptability threshold based on the sensitivity levels;

determine, via the computer-implemented scheduling system, that the event risk is higher than the adjusted the event risk to the risk acceptability threshold; and automatically implement, via the computer-implemented scheduling system, a second risk mitigation policy in response to the determining that the event risk is higher than the adjusted risk acceptability threshold, wherein the implementing comprises:
modifying the scheduling request; and
outputting a response to the scheduling request via the user interface, wherein the response includes a recommended change to the event.

14. The computer program product of claim 13, wherein the location risk characteristics include:
a number of visitors that have entered the location over a duration; and
a maximum number of visitors in the location simultaneously over the duration.

15. The computer program product of claim 13, wherein the instructions further cause the computer to:
determine, based on the location risk metrics, that a risk constraint has been violated; and
automatically generate, based on the determination that the risk constraint has been violated, a risk report.

16. The method of claim 1, wherein implementing the second risk mitigation policy includes executing at least one action selected from the group consisting of:
automatically restricting access, by the computer-implemented scheduling system, to the location;
proposing, in the response output by the computer-implemented scheduling system, an alternative location for the event as the recommended change;
generating, by the computer-implemented scheduling system, a route through the region to the selected location based on the floorplan, the continuously tracked location risk characteristics, and a location of a user at the time of the event;
generating, by the computer-implemented scheduling system, a visual message or audible alert that communicates, via a mobile computing device, that the event risk is greater than the risk acceptability threshold; and
adjusting, by the computer-implemented scheduling system, the number of predicted attendees of the event, wherein the adjusting comprises:
sending an alert communicating a location risk metric to mobile devices of the predicted attendees;
receiving, from the mobile devices, at least one response to the alert; and
updating the number of the predicted attendees based on the at least one response.

17. The method of claim 1, further comprising:
monitoring risk metrics of the region based on the image data and the audio data; and
generating risk mitigation proposals based on the risk metrics.

18. The method of claim 2, wherein the computer-implemented scheduling system determines the number of previous visitors based on the sensor data from the motion sensor.

19. The method of claim 3, wherein the computer-implemented scheduling system determines the likelihood based on the sensor data from the cameras and the microphones.

20. The method of claim 3, further comprising automatically generating, by the computer-implemented scheduling system, periodic risk reports for the region based on the location risk metrics.

* * * * *